United States Patent [19]

Benedict

[11] 4,135,387

[45] Jan. 23, 1979

[54] DEVICE FOR MONITORING PHASE PROPORTIONS OF A SINGLE COMPONENT FLUID

[75] Inventor: Robert P. Benedict, Media, Pa.

[73] Assignee: Westinghouse Electric Corp., Pittsburgh, Pa.

[21] Appl. No.: 823,483

[22] Filed: Aug. 10, 1977

[51] Int. Cl.² ............................................. G01N 29/02
[52] U.S. Cl. ......................................... 73/53; 73/597
[58] Field of Search .................. 73/19, 53, 61 R, 597, 73/599

[56] References Cited

U.S. PATENT DOCUMENTS

| 3,486,370 | 12/1969 | Chedeville et al. | 73/597 |
| 3,791,200 | 2/1974 | Hayre | 73/61 R X |
| 3,923,415 | 12/1975 | Benedict | 415/1 |
| 3,973,430 | 8/1976 | Cirulis et al. | 73/597 X |

Primary Examiner—Charles A. Ruehl
Attorney, Agent, or Firm—J. W. Keen

[57] ABSTRACT

An apparatus and method for providing continuous phase proportion indications for a single component fluid having multiple coexisting phases. The apparatus assures homogeneity of the multiple phases by subjecting the fluid to an ultrasonic or sonic wave generator which uniformly disperses the phases among each other. The homogeneous phase mixture is exposed to a second sonic or ultrasonic wave generator with the speed of the wave originating therefrom being timed during its traversal across the mixture. Such timing enables determination of the acoustic velocity which, in addition to the wave's frequency and mixture's pressure, temperature and drop size can be correlated with the proportions of the phases in the mixture.

1 Claim, 6 Drawing Figures

DEVICE FOR MONITORING PHASE PROPORTIONS OF A SINGLE COMPONENT FLUID

BACKGROUND OF THE INVENTION

1. Field of the Invention

This invention relates to measurement of relative phase proportions for single component fluids having multiple coexisting phases, and more particularly, to an apparatus and method for determining the quality of a steam-water mixture.

2. Description of the Prior Art

In large steam turbines and associated power generation equipment which have steam-water mixtures flowing therethrough it is highly desirable to obtain continuous quality measurements. Such quality measurements are necessary to determine thermodynamic performance and provide early warning indications of malfunctioning power generation equipment. Thermodynamic state points used to gauge turbine performance can be determined by temperature and pressure measurements when the steam is in the "dry" thermodynamic region. Thus, quality measurements of steam in fossil-fueled steam turbines are often necessitated only near the turbines' exhaust ends since the quality of the steam passing therethrough falls into the "wet" thermodynamic region only in the later, lower pressure stages of the turbines. Because nuclear-fueled steam turbines typically operate at lower pressures, wet steam is encountered in correspondingly earlier stages and thus require a more extensive number of quality determinations to accurately monitor their performance.

Previously, throttling and separating calorimeters were used to provide quality measurements on an intermittent or discrete time basis. However, calorimetry methods of quality measurement have recently fallen into disrepute and hence disuse because of serious questions raised as to the adequacy of the sampling procedures applied to the steam-water mixture. Since Pitot-type probes were often used to draw off samples of the steam-water mixture, radial traverses across the mixture were required to establish average qualities. More recently, in ASME Paper No. 72-WA/PTC-1 entitled "ASME Steam Turbine Code Test Using Radioactive Tracers", radioactive techniques have been set out as establishing steam quality. The results from such tests were also judged to be questionable since this method requires that elaborate safety precautions be taken in handling radioactive-decaying fluids, injecting them into the mixture, withdrawing samples of such fluids from the mixture at the point in question, and performing complex half-life calculations.

Disadvantages of all the previously mentioned quality measurement techniques include their inability to provide continuous quality monitoring and yield reliable quality determinations.

SUMMARY OF THE INVENTION

In accordance with the present invention an improved apparatus and method is provided for measuring relative phase proportions coexisting in a single component fluid. The invention generally comprises a means for uniformly dispersing the coexisting phases through each other to insure a homogeneous fluid and means for measuring acoustic velocity through such homogeneous fluid. When used with the acoustic frequency, fluid temperature, pressure and drop size, the acoustic velocity determination can be directly correlated with the relative phase proportions which, for water, are better known as quality.

The method for monitoring coexisting phase proportions in a single component fluid comprises dispersing the phases uniformly among each other to provide a homogeneous fluid, passing an acoustic signal through such homogeneous fluid, and measuring the time required for such signal to pass through such homogeneous fluid. The acoustic velocity determined from such timing can also be correlated with relative phase proportions.

Such apparatus and method for measuring the relative phase proportions can provide continuous indications of the thermodynamic state of the fluid and/or the performance of a machine utilizing such fluid.

BRIEF DESCRIPTION OF THE DRAWINGS

The invention will be more fully understood from the following detailed description of a preferred embodiment, taken in connection with the accompanying drawings, in which.

DESCRIPTION OF THE PREFERRED EMBODIMENT

The present invention is concerned primarily with monitoring coexisting phase proportions in single component fluids. Accordingly, in the description which follows, the invention is shown attached to a conduit which carries a mixture of steam and water. It should be understood, however, that the invention may be utilized for other fluids whose phase proportions can be correlated with, among other parameters, acoustic velocity and may also be utilized on other apparatus which have single component fluids whose phases are non-homogeneously distributed therethrough.

Figure 1:
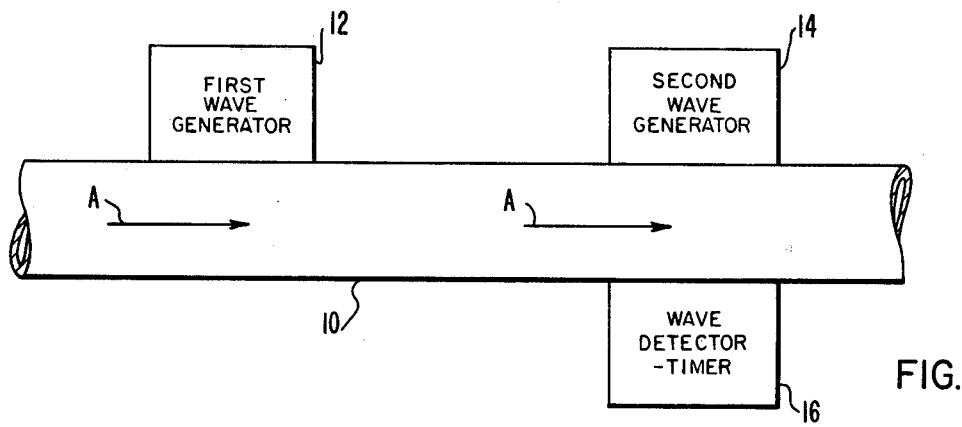
FIG. 1 is a schematic of a conduit carrying a multiphase fluid with a dispersing means situated upstream from an acoustic velocity measurement device.

In FIG. 1 the invention is shown in operating position attached to conduit 10. Conduit 10, as previously stated, may also be considered, for the purposes of this invention, a device such as a steam turbine, crossover pipe connecting sections of such a steam turbine, extraction conduit, or other device. Arrows A indicate the normal direction of flow of the single component fluid in question. After the multiple phase fluid has been subjected to sonic or ultrasonic waves from a first wave generator 12, the fluid whose homogeneity has now been insured is exposed to more sonic or ultrasonic waves generated by a second wave generator 14. The acoustic waves generated by generator 14 are detected by detector 16 which also times the waves' traversal through the fluid, but it is to be understood that the timing mechanism which determines the acoustic velocity need not be integral with the wave detector. The multiphase fluid flowing through conduit 10 has a flow direction indicated by arrows A. Fluid flow through conduit 10 is used to insure acoustic velocity measurement through a homogeneous fluid since wave generator 12, situated upstream from wave generator 14 and detector 16, causes uniform phase dispersal.

Figure 2A:
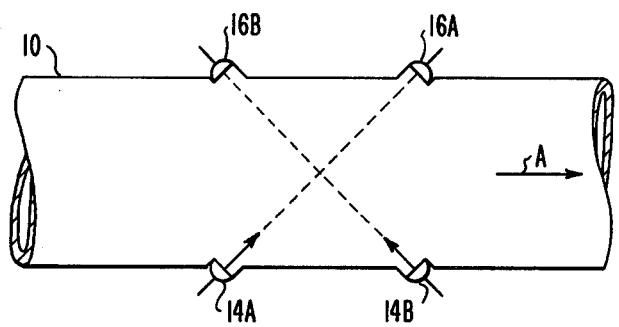
FIGS. 2A and 2B schematically illustrate the acoustic signal sources and acoustic receivers are exemplary embodiments for measuring acoustic velocity through an intervening multiphase fluid.
Figure 2B:
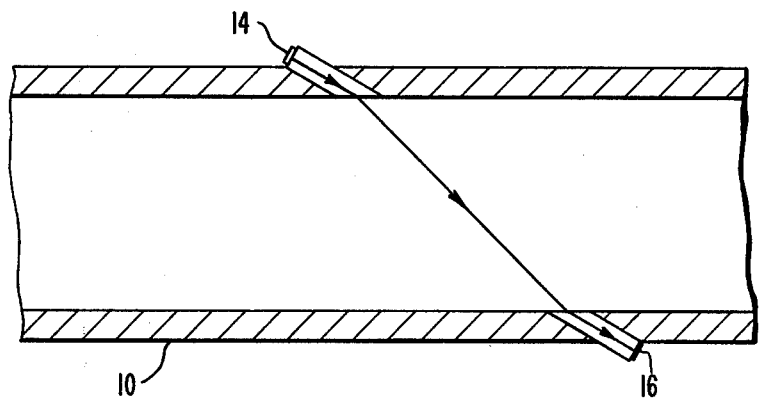

FIGS. 2A and 2B illustrate two alternate techniques for measuring acoustic velocity through a fluid. FIG. 2A, known as the "travel time difference method", utilizes sending transducers 14A and 14B which transmit acoustic waves upstream and downstream respectively to receiving transducers 16A and 16B. FIG. 2B illustrates an apparatus embodying the so-called Leading Edge Method which is used in Westinghouse Leading Edge Flowmeter Model 601 for measuring acoustic velocity. Since the acoustic velocity measurement techniques mentioned are not exhaustive, other acoustic velocity measuring techniques are also considered to be encompassed by the present invention.

In general, the process of acoustic wave propagation in multiphase, single component fluids is a function of phase proportions, fluid pressure, droplet size, distribution, and frequency of the acoustic wave.

Figure 3A:
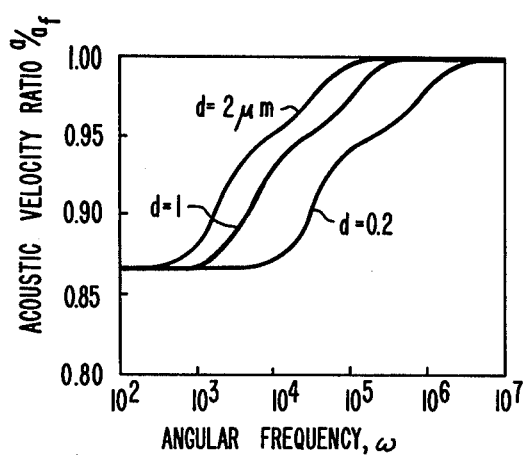
FIGS. 3A, 3B, and 3C are plots of acoustic velocity ratio versus angular acoustic frequency for various droplet sizes, wetness fractions, and pressures, respectively.
Figure 3B:
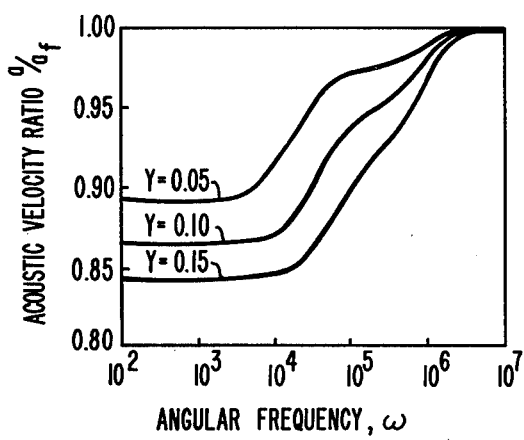
Figure 3C:
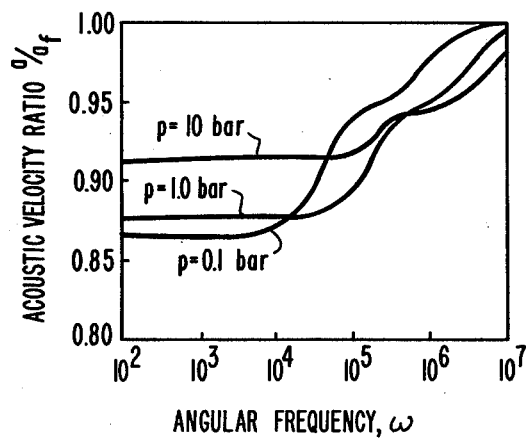

Acoustic velocity, once known, can be correlated with the previously mentioned parameters to obtain the fluid's phase proportions. FIGS. 3A, 3B, and 3C taken from a paper entitled, "Gas Dynamics of Two-Phase Media and Energy Losses Due to Wet Steam" by M. J. Moore and published in May 1974, illustrate a correlation of acoustic velocity ratios as a function of the aforementioned fluid parameters. It is to be noted that each of the FIGS. 3A, 3B, and 3C maintain two of the parameters as constants because of the high complexity of any plot resulting from inclusion of all parameters in a single plot. Depending on the specific circumstances, it may be convenient to use apparatus which have certain constant parameters such as a constant frequency and droplet size. Actual correlations based on a particular multiphase fluid in question whose phases have been homogenized by sonic or ultrasonic dispersion can be developed and the apparatus calibrated based on the degree of homogeneity available from such dispersion.

While most components of the present invention comprise separate pieces of prior art which are each commercially available combining the separate components in a manner consistent with this disclosure enables continuous monitoring of coexisting phase proportions in single component fluids such as steam quality in steam power generation equipment. It will be apparent that use of such apparatus and method will provide much sought-after continuous equipment performance indications and diagnostic signaling of equipment malfunctions.

I claim:

1. An apparatus for monitoring coexisting phase proportions in single component fluids, said apparatus comprising:
    a first acoustic wave generator for passing acoustic signals through said fluid for dispersing the coexisting phases through each other to insure a homogeneous fluid; and
    a second acoustic wave generator for passing acoustic signals through said homogeneous fluid;
    means associated with said second acoustic wave generator for detecting waves generated thereby; and
    means for timing the traversal of the waves generated by said second acoustic wave generator from the second acoustic wave generator to the detecting means.

* * * * *